United States Patent [19]

Parekh et al.

[11] Patent Number: 5,539,090
[45] Date of Patent: Jul. 23, 1996

[54] RELEASE AND ISOLATION OF N-GLYCANS AND O-GLYCANS

[75] Inventors: Rajesh B. Parekh, Kirtlington; Anthony H. Merry, Charlbury; James Bruce, Eynsham, all of England

[73] Assignee: Oxford GlycoSystems Limited, Abingdon, United Kingdom

[21] Appl. No.: 195,761

[22] Filed: Mar. 12, 1993

Related U.S. Application Data

[63] Continuation of Ser. No. 719,287, Jun. 21, 1991, abandoned.

[30] Foreign Application Priority Data

Jun. 21, 1990 [GB] United Kingdom .................. 9013828

[51] Int. Cl.[6] .............................. C07H 5/04; C07H 5/06; C07H 1/00; C08B 37/00
[52] U.S. Cl. ................. 536/17.9; 536/18.7; 536/22.1; 536/55.2; 536/55.3; 536/124
[58] Field of Search .......................... 536/124, 4.1, 17.9, 536/18.7, 22, 55.3, 55.2

[56] References Cited

U.S. PATENT DOCUMENTS 4,719,294  1/1988  Rademacher et al. .................. 536/18.7
4,736,022  4/1988  Rademacher et al. .................. 536/18.7

FOREIGN PATENT DOCUMENTS 37165    12/1984  Australia .
0149163  12/1984  European Pat. Off. .
0215766   3/1987  European Pat. Off. .

OTHER PUBLICATIONS

J. Montreuil et al., "Carbohydrate Analysis—A Practical Approach," IRL Press 1986.

CARBOHYDRATE RESEARCH, vol. 151, 1986, pp. 89–103, B. Bendiak et al "Purification of Oligosaccharides Having a Free Reducing-end from Glycopeptide Sources".

*Primary Examiner*—Douglas W. Robinson
*Assistant Examiner*—Everett White
*Attorney, Agent, or Firm*—Nixon & Vanderhye

[57] ABSTRACT

N- and O-glycans are released from a glycoconjugate with a substantially anhydrous hydrazine reagent, the glycoconjugate being substantially salt-free and substantially anhydrous. Released N- and O-glycans are recovered in substantially unreduced and intact form using a chromatographic material.

20 Claims, 9 Drawing Sheets

RELEASE AND ISOLATION OF N-GLYCANS AND O-GLYCANS

This is a continuation of application Ser. No. 07/719,287, filed Jun. 21, 1991, now abandoned.

BACKGROUND OF THE INVENTION

This invention relates to a method for the release of N-glycans and O-glycans (i.e. 'N- and O-linked type' oligosaccharides) from glycoconjugates and to isolation of such glycans.

Examples of glycoconjugates are glycoproteins, glycohormones and glycolipids.

An 'N-linked type' oligosaccharide is an oligosaccharide which is covalently bonded to a conjugate by an N-glycosidic linkage, and an 'O-linked type' oligosaccharide is an oligosaccharide which is bonded to a conjugate by an O-glycosidic linkage. An example of such linkages as typically found on glycoproteins is shown in FIG. 1 of the accompanying Drawings. For the purposes of this disclosure, release refers to an event or process leading to cleavage of the covalent N- and O-glycosidic bonds attaching 'N-' and 'O-linked-type' oligosaccharides to a conjugate, and isolation refers to an event or process leading to physical separation of released oligosaccharides from conjugate or conjugate-derived materials.

The release and subsequent isolation of 'N- and O-linked type' oligosaccharides (hereinafter referred to respectively as N- and O-glycans) from a glycoconjugate are important for several reasons. Principal among these are the following: Firstly, a detailed structural characterization of a glycoconjugate requires structural analysis of any associated glycans. Since several such glycans may be attached to a single conjugate, and since structural analysis of glycans is most accurately performed on single, purified glycans, such an analysis requires prior release of such glycans from the conjugate and subsequent isolation of such glycans from the conjugate, and then purification of glycans from one another. Secondly, such glycans are increasingly recognized as important biological molecules in their own right. A study of the biological properties of N- and O-glycans is preferentially undertaken using N- and O-glycans free of the conjugate. The criteria that ought to be simultaneously satisfied for any successful method for the release and isolation of N- and O-glycans from a glycoconjugate are as follows:

(i) The method of release should preferably cleave the N- and O-glycosidic linkage in a manner independent of the nature of both the oligosaccharide component and the conjugate component.

(ii) The method of release should preferably achieve cleavage without permanent (i.e. not easily reversible) chemical damage to the cleaved glycans.

(iii) The method of isolation should preferably separate N- and O-glycans from a conjugate in a manner independent of the nature of both the oligosaccharide component and the conjugate component, as in (i), above.

(iv) The method of isolation should preferably achieve isolation without causing chemical damage to the cleaved glycans.

In addition, it is preferable if the method also achieves recovery in high yield (e.g. $\geq 85\%$) of released N- and O-glycans, irrespective of the amount of starting glycoconjugate.

Previously, two different methods have been used for the release of both N- and O-glycans. These are briefly summarized below and assessed with respect to the above criteria.

A. Enzymatic Methods—For example, the use of proteolytic enzymes such as Pronase® to obtain glycopeptides from glycoproteins, and/or the use of a mixture of enzymes such as O-glycanase™ (E.C. number 3.2.1.97) to cleave some O-glycans from the glycoconjugate and N-glycanase™ (E.C. number 3.2.2.18) to cleave some O-glycans from the conjugate. Such methods are generally unsatisfactory for several reasons, but principally because of the selectivity of glycan release. Enzymes are, by their very nature specific, and release only certain glycans and then in a manner influenced by the attached conjugate. That is, enzymatic methods as currently practiced and understood, do not satisfy criterion (i), above.

B. Chemical Methods—Two chemical methods have been practiced for the release of N- and O-glycans. These are:

(i) The use of alkaline solutions. The N- and O-glycosidic linkages attaching N- and O-glycans to a conjugate are alkali labile, and alkaline solutions can therefore be employed for release of N- and O-glycans. For example, incubation with 1M NaOH at 100° C. for 4 hours has been successfully employed. An established and accepted disadvantage of this method is the alkalilability of most N- and O-glycans. Most N- and O-glycans that are attached to a peptide are so attached through the structures shown in FIG. 2 of the accompanying Drawings. Upon cleavage (FIG. 2) by alkali, the reducing terminus monosaccharide residue (N-acetylglucosamine or GlcNAc in N-glycans, and N-acetylgalactosamine or GalNAc in O-glycans) is further degraded by the alkali. Such degradation can be prevented by the reduction of the reducing terminus residue by performing the alkali-induced release in the presence of a vast excess of reducing agent. Typically 4M $NaBH_4$ is used. This reduction involves conversion of the released glycans to the alditol form (FIG. 2). Irrespective, therefore, of the presence or absence of excess reducing agent, the released glycans will be recovered in a permanently chemically altered form (i.e. not as the native compound). This method does not therefore satisfy criterion (ii), above.

(ii) The use of anydrous hydrazine. A few reports in the scientific literature concerning O-glycans suggest that O-glycans may be released from a peptide conjugate after incubating an anhydrous glycoprotein at high temperature (typically 100° C.) for several hours (typically $\geq 10$ hours) with anhydrous hydrazine. Each such report also indicates that any O-glycans so released are subject to extensive chemical degradation and alteration of the released O-glycans by the hydrazine. Indeed, the general scientific opinion indicates that: 'The behavior towards hydrazine of O-glycosidically linked glycans has not yet been elucidated. However some results show that they are profoundly degraded until an alkali-stable linkage stops the 'peeling' relaction.' (J. Montreuil et al., in 'Carbohydrate Analysis—A Practical Approach'—Ed. M. F. Chaplin and J. F. Kennedy—IRL Press, 1986). With regard to N-glycans, numerous authors have studied the release by hydrazinolysis of N-glycans from glycoproteins. The currently preferred method is that of Rademacher and Dwek (European Patent Application no. 0 215 766A2). This method, addressing only N-glycans, is a method in which a set of conditions were defined allowing recovery of N-glycans in undefined yield, but intact with respect to structure. The method of Rademacher and Dwek was therefore an improvement on all previous methods, but as shown by the results disclosed in this specification, gives a relatively lower yield of N-glycans and would, when applied to gycloproteins containing O-glycans, lead to the recovery of degraded (i.e. chemically altered) O-glycans. These consequences arise from the fact that the study of Rademacher and Dwek did not consider O-glycans (i.e. considered glycoproteins with only N-glycans). Hence this method as currently practiced is not generally applicable to the recovery of intact N- and O-glycans from a glycoprotein sample.

In summary, none of the above mentioned methods as currently practiced and understood is suitable for the release of intact, unaltered, N- and O-glycans.

BRIEF DESCRIPTION OF THE INVENTION

In accordance with one aspect of the present invention there is provided a method for releasing N- and O-glycans from a glycoconjugate which includes subjecting a glycoconjugate to the influence of a hydrazine reagent, said glycoconjugate being substantially salt-free and substantially anhydrous and said hydrazine reagent being substantially anhydrous, and controlling conditions under which the glycoconjugate is subjected to the influence of the hydrazine reagent so as to cause release of N- and O-glycans from the glycoconjugate in such a way as to allow subsequent recovery of N- and O-glycans in substantially unreduced and intact form.

In one embodiment the present invention may be used to achieve a high yield of N- and O-glycans.

In accordance with the present invention a high yield may be defined as $\geq 85\%$, but may be less than this as long as the yield is useful in practice.

The glycoconjugate optionally may be subjected to the influence of the hydrazine reagent and subjected to an energy input. Thus, for example, glycoconjugate and the hydrazine reagent may be brought together and the resulting reaction mixture heated by any suitable means. Other forms of energy input may be employed if desired (e.g. microwave radiation or infra-red radiation).

The hydrazine reagent may be hydrazine itself or any suitable derivative or compound thereof (e.g. related salt) capable of bringing about a desired cleavage of an N-glycosidic and an O-glycosidic bond linking an N- and O-glycan to a conjugate. The hydrazine reagent may be used, for example, in liquid form or in vapor form.

By way of example, the present invention provides a method for releasing unreduced and intact N- and O-glycans from glycoconjugates, which comprises heating a substantially salt-free and essentially anhydrous glyconjugate with principally anhydrous hydrazine reagent under optimal conditions so as to cause release from the conjugate of N- and O-glycans in such a way as to allow the subsequent recovery of such glycans in intact form.

The term "salt-free" as used in this Specification means not containing salt to an extent which leads to any unacceptable interference with the performance of a method in accordance with the present invention (e.g. release of N- and O-glycans from a glycoconjugate).

The term "anhydrous" as used in this Specification means not containing water to an extent which leads to any unacceptable interference with the performance of a method in accordance with the present invention (e.g. release of N- and O-glycans from a glycoconjugate).

The heating may be effected either microscopically or macroscopically.

In one embodiment the method of the present invention may include the step of removing salt from a glycoconjugate prior to subjecting it to the influence of a hydrazine reagent.

In another embodiment the method of the present invention may include the step of removing water from a glycoconjugate prior to subjecting it to the influence of a hydrazine reagent.

The invention also provides a method for the release of N- and O-glycans from a glycoconjugate which method includes a step of isolating intact and unreduced N- and O-glycans.

Following release, it is preferable that any remaining, unreacted hydrazine reagent is removed to leave, as an unfractionated pool, the total population of N- and O-glycans released.

It is also preferable that chromatographic procedures be performed to achieve substantial removal of conjugate or conjugate-derived material from N- and O-glycans, to leave N- and O-glycans as an unfractionated pool free of such material.

With certain glycans, it may be necessary to perform an N-acetylation reaction involving N-acetylation of any of the free amino groups produced as a result of a reaction with hydrazine. Without prior knowledge of the full structure of glycans involved, it is difficult to predict in advance whether such N-acetylation will be necessary. It is therefore preferable to perform this reaction as a precautionary measure, in all cases.

It is also preferable that N-acetylated isolated N- and O-glycans be subjected to acidic conditions (whether through the use of acid in immobilized form, mineral acid, or Lewis acid) to cleave any acetohydrazone derivatives that may form during the reaction, and so to regenerate the intact, unaltered N- and O-glycans.

The present invention also provides a method for the release of N- and O-glycans which also includes isolation of N- and O-glycans which method includes the steps of subjecting a glycoconjugate to the influence of a hydrazine reagent, said glycoconjugate being substantially salt-free and substantially anhydrous and said hydrazine reagent being substantially anhydrous, controlling conditions under which the glycoconjugate is subjected to the influence of the hydrazine reagent so as to cause release of N- and O-glycans from the glycoconjugate in such a way as to allow subsequent recovery of N- and O-glycans in substantially unreduced and intact form, contacting the reaction mixture, formed by subjecting the glycoconjugate to the influence of the hydrazine reagent, with a first chromatographic material thereby to effect sorbing of N-glycan and O-glycan (and any derivatives thereof) upon the chromatographic material, eluting the chromatographic material, said sorbing and said eluting being such as to effect separation of N-glycan and O-glycan (and any derivative thereof) from conjugate and/or conjugate-derived material and such as to remove any hydrazine reagent, and, if a derivative of an N- and O-glycan is present which has free primary amino acid groups, performing an N-acetylation reaction to generate unreduced glycan from the derivative, and, if required by the manner in which any N-acetylation reaction was carried out, removing mono- and/or di-valent cations from a reaction mixture obtained after the N-acetylation reaction, and separating from such a reaction mixture N- and O-glycans, or a derivative thereof, by means of sorption upon a second chromatographic material and selective elution therefrom, and converting any derivative of the N- and O-glycans to unreduced form.

By way of example, an N-acetylation reaction may be performed either before or after desorption from the first chromatographic material.

Also, by way of example, where any derivative of the N- and O-glycan obtained after elution from the second chromatographic material is an acetohydrazone derivative mildly acidic conditions may be used to effect generation of unreduced N- and O-glycan.

DETAILED DESCRIPTION OF THE INVENTION

Figure 1:
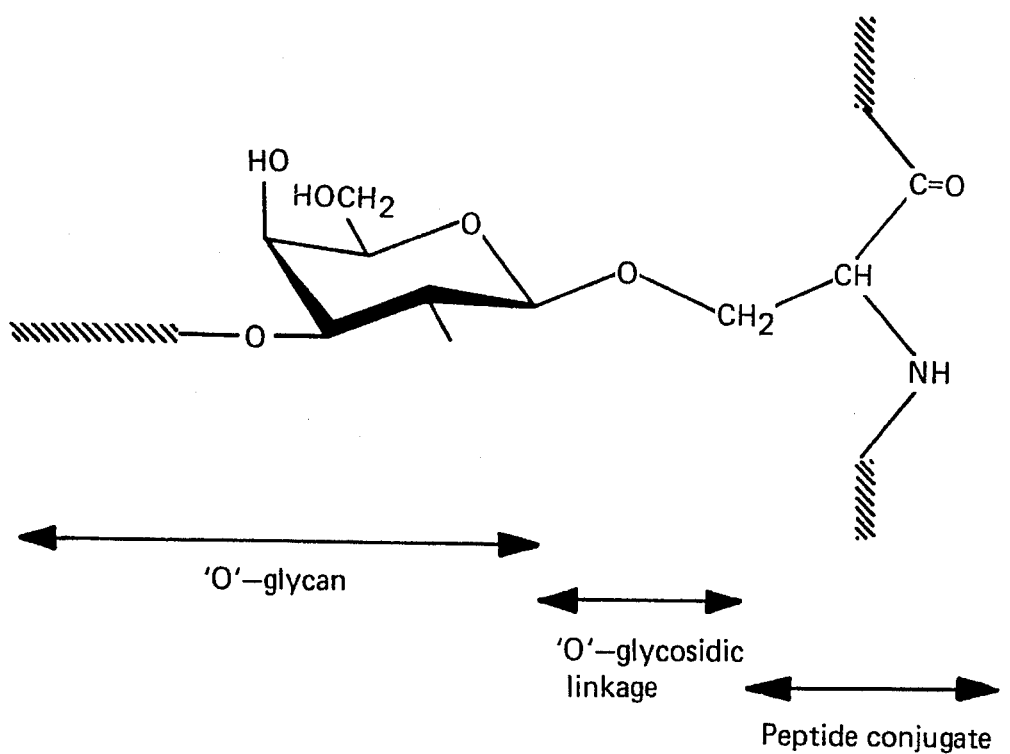
Figure 1:
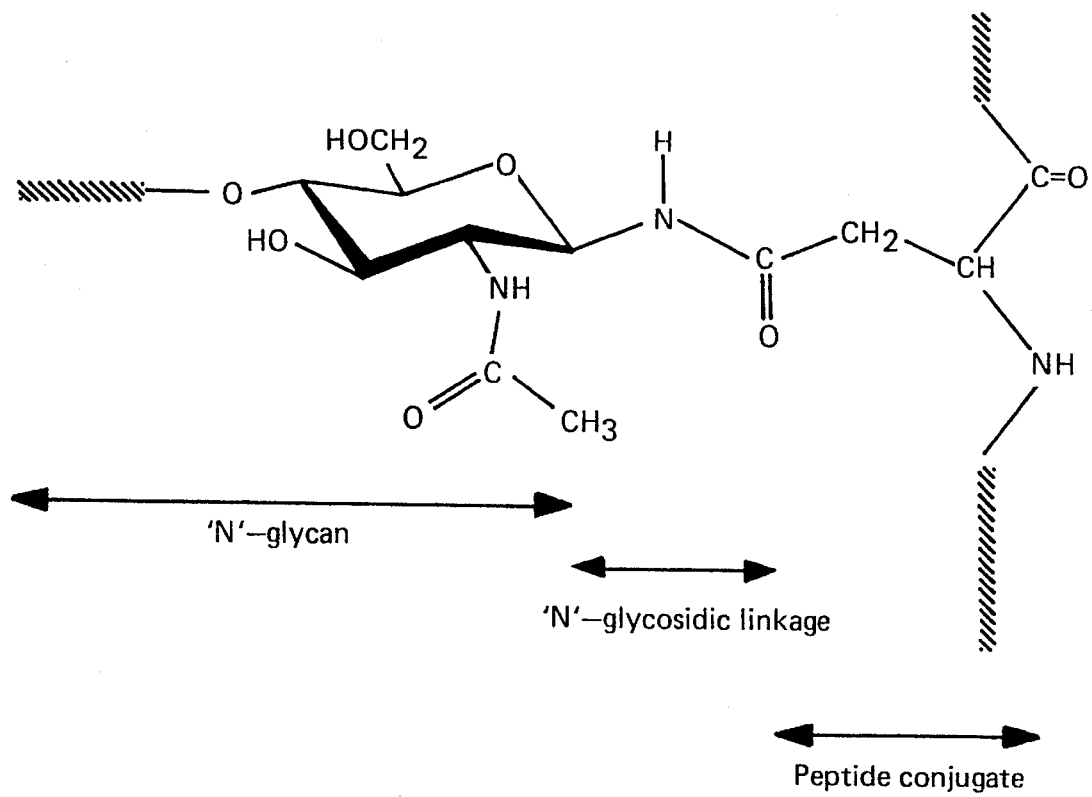

The invention can be applied to glycoconjugates in general, however, by way of exemplification reference will later be made to a specific example namely bovine fetuin, which is accepted in the scientific literature as a model glycoprotein for study, containing as it does, N- and O-glycans.

Before subjecting the glycoconjugate to the influence of the hydrazine reagent (i.e. hydrazinolysis), the glycoconjugate and hydrazine reagent are preferably prepared as follows. The glycoconjugate is rendered essentially salt-free, for example by dialysis, gel filtration, or chromatography in a suitable system. Once salt-free, the glycoconjugate is rendered essentially anhydrous, for example by lyophilization, and the water content reduced to at least that achieved at equilibrium under lyophilization conditions of 25 millibar at 25° C. The water content of the hydrazine reagent is likewise relevant, and should not exceed 4% volume/volume. Thus most commercially available samples of anhydrous hydrazine reagent are suitable, though drying of hydrazine reagent can be achieved through one of numerous reported processes. Suitable hydrazine reagent is then added to the appropriately prepared sample in an air-tight vessel. The reaction between glycoconjugate and hydrazine reagent can be initiated by the input of energy, either microscopically or macroscopically, for example by raising the temperature. For any method of input of energy the optimal conditions for reaction can be deduced from various experimental approaches. In this disclosure the preferred method of initiating the reaction is through increase in temperature to a steady state.

By experimental measurement of yield at various temperatures over time it has been shown, in accordance with the present invention, that reaction of a glycoconjugate with a hydrazine reagent to release N- and O-glycans follows first-order reaction kinetics.

The preferred theoretical framework therefore for analysis of experimental results is the Arrhenius equation, which is commonly used to define to a first approximation the dependence of the rate of a reaction on temperature. This form is as follows:

$$k = Ae^{-E_{ACT}/RT}$$

where
 k=reaction rate
 A=Arrhenius constant
 R=Universal gas constant
 $E_{ACT}$=Activation energy
 T=temperature.

In any such chemical reaction in which N- and O-glycans are released, and the released N- and O-glycans then subject to an additional degradative reaction, it is deduced from the Arrhenius equation that:

mole fraction of O-glycans released in intact form =

$$m_O = [e^{-(A_{do}e^{-E^D_O/RT}) \cdot t}] - [e^{-(A_{ro}e^{-E^R_O/RT}) \cdot t}]$$

mole fraction of N-glycans released in intact form =

$$m_N = -[e^{-(A_{rN}e^{-E^A_N/RT}) \cdot t}] + [e^{-(A_{DN}e^{-E^D_N/RT}) \cdot t}]$$

where
 e=natural antilogarithm
 $A_{ro}$=Arrhenius constant for release of O-glycans
 $A_{do}$=Arrhenius constant for degradation of O-glycans
 $E^R_O$=Activation energy for release of O-glycans
 $E_{DO}$=Activation energy for degradation of O-glycans
 $A_{rN}$=Arrhenius constant for the release of O-glycans
 $A_{DN}$=Arrhenius constant for the degradation of N-glycans
 $E^A_N$=Activation energy for the release of N-glycans
 $E^D_N$=Activation energy for the degradation of N-glycans
 R=Universal gas constant
 T=Temperature
 t=time Conditions may be selected in accordance with the above equation such as to achieve a preselected yield of intact N- and O-glycans (e.g. a yield such as ≧85%).

Although a preferred yield is a high yield such as ≧85% there may be applications where lower yields are acceptable and conditions which give rise to such lower yields may be selected in accordance with the above equation.

Conditions of temperature and time suitable for release of intact N- and O-glycans can be deduced from experiments in which the release of intact N- and O-glycans is measured as a function of temperature only, since such experiments allow a determination of $A_{ro}$, $A_{do}$, $E^R_O$, $E^D_O$, $A_{rN}$, $A_{dN}$, $E^A_N$ and $E^D_N$. The results of such an experiment are shown in FIG. 3 of the accompanying Drawings in which the relative release of intact N- and O-glycans is measured after incubation of the glycoprotein bovine fetuin with suitable hydrazine for 8 hours at various temperatures.

Figure 3:
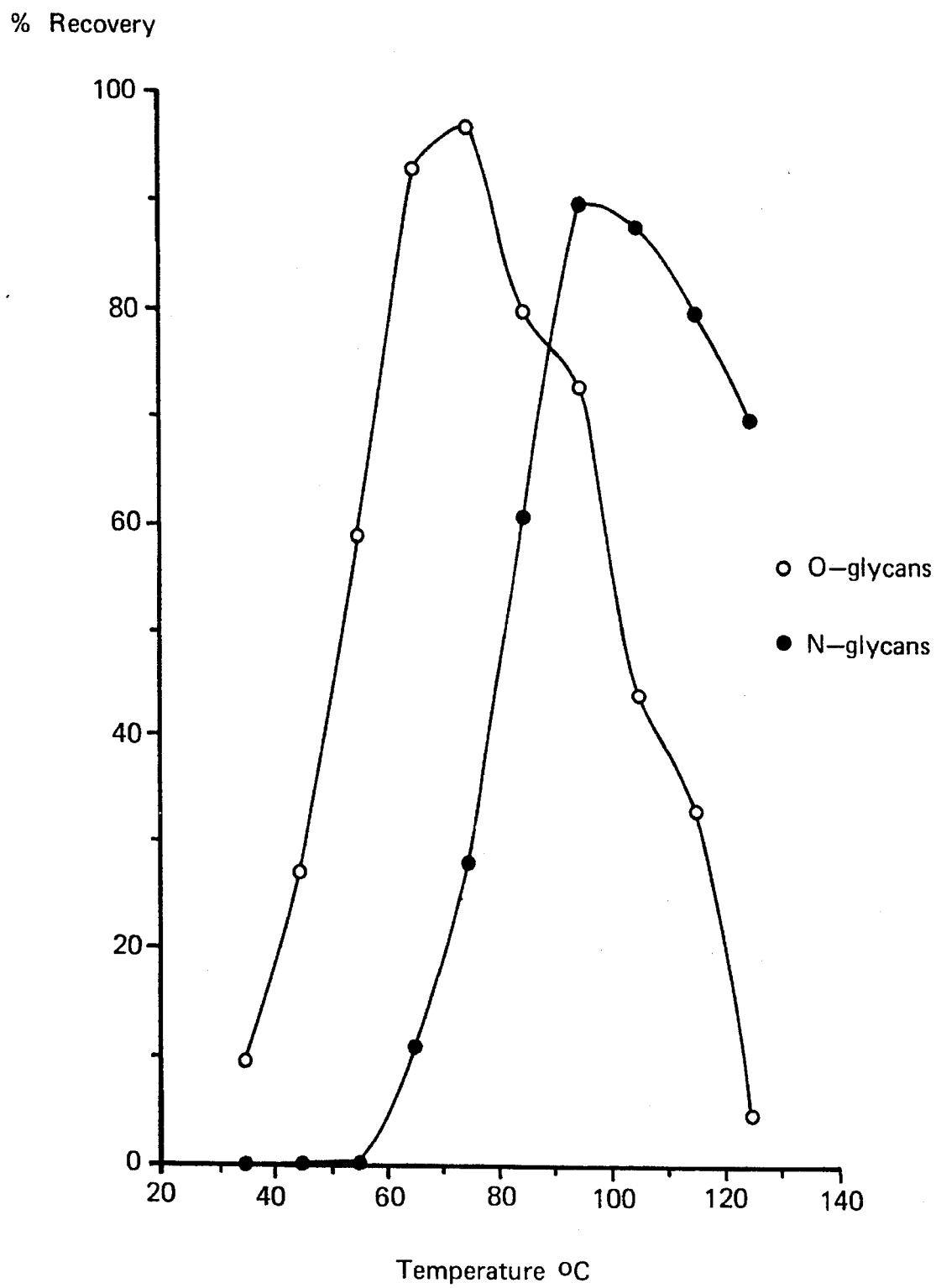

From the data presented in FIG. 3, the approximate conditions of temperature and time required for any given percentage recovery of intact N- or O-glycans can be calculated. Examples of such calculations for O-glycans are summarized in FIG. 4A of the accompanying Drawings, and for N-glycans in FIG. 4B of the accompanying Drawings. In the case of O-glycans the relative rates of release and destruction are such that the conditions for recovery of a given percentage of O-glycans is defined by a region on the temperature/time graph that is FIG. 4A. For example, only the conditions of temperature and time defined by points between lines L-1 and L-4 will allow >94% recovery of intact O-glycans, and similarly only the conditions defined by points between lines L-3 and L-2 will allow >90% recovery of intact O-glycans, and so on. In the case of N-glycans, destruction does not occur over the conditions defined by the curves in FIG. 4B, but only under temperature conditions >105 Celsius and time >4 hours. By comparing the data in FIGS. 4A and 4B, it is seen that the range of conditions under which recovery in high yield (e.g. ≧85%) recovery of both N- and O-glycans can be obtained under these experimental conditions is restricted to the shaded area in FIG. 4C of the accompanying Drawings. As is depicted in FIG. 4C, the temperature range under these experimental conditions is from about 95° C. to about 105° C., and a time at temperature of from about 1 hour to about 5 hours. The conditions, included within this area, used in this disclosure are 95 Celsius for 3.75 hours. Similar analyses can be used to define reaction conditions for other forms of initiation of the reaction.

At this point the reaction to achieve successfully the release of N- and O-glycans from glycoconjugate is complete. For further study and analysis of unreleased glycans it is preferable that the glycans be first isolated from unreacted hydrazine reagent and conjugate or conjugate-derived material. After the incubation, unreacted hydrazine reagent can be removed in one of two ways. Firstly, by evaporation under reduced pressure, followed by repetitive co-evaporation with a miscible agent (such as anhydrous toluene). Secondly, and the preferred method as described in this Specification, by the adsorption of the glycans in the reaction mixture to a chromatographic medium, of which the preferred medium in this Specification is a cellulose-based substance, so as to remove unreacted hydrazine reagent and also substantially remove conjugate or conjugate-derived material from released glycans without repeated manipulation of the glycans, without selective loss of yield of released glycan, and without the introduction of contaminant material. This is performed as follows:

To a column of microcrystalline cellulose (a commercially available example of which is Avicel®) equilibrated in a suitable extraction solvent an example of which is butanol, ethanol, and acetic acid (varying between 4:1:0.01–0.6 (v/v/v)), the reaction mixture is applied. The N- and O-glycans and some contaminants are adsorbed to the cellulose particles, and the hydrazine reagent eluted away using the extraction solvent (typically three column washes of solvent are required), and the N- and O-glycans desorbed (and so eluted) with the use of methanol and water or desired aqueous buffer (typically 2–3 column volumes).

The N- and O-glycans so obtained may contain a proportion of free primary amino groups. These groups can therefore be N-acetylated, if desired, to generate the authentic unreduced N- and O-glycans. Numerous methods have been reported for performing such N-acetylation. In a preferred embodiment, the N- and O-glycans are N-acetylated by reaction with excess acetic anhydride in either the methanol/water mixture or aqueous sodium acetate buffer solution, pH 5.0. Such N-acetylation can be performed at any temperature between 0° C. and 37° C. with no loss of efficiency and quantitative N-acetylation occurs in ~30 minutes. The use of methanol/water or sodium acetate solution are preferred since either can be used to elute the N- and O-glycans from the cellulose column used for hydrazine reagent removal, thus avoiding any manipulation of the sample prior to N-acetylation. In those instances where aqueous buffer containing monovalent cations are used, such cations are removed by passage of the N-acetylation mixture through a strong cation exchange resin in the proton form. Numerous such resins are available and suitable, but a preferred resin is Dowex AG50X12 ($H^+$), a styrene/divinyl benzene polymeric lattice carrying sulphonic acid functional groups. In those instances where aqueous buffer containing mono- and/or di-valent cations are used, a mixed-bed column containing sufficient resins to remove both such ions is used. This would typically require the use of Chelex 100 ($Na^+$) to remove divalent cations, and Dowex AG50X12 ($H^+$) to remove monovalent cations. In those instances where N-acetylation is performed in the absence of cations, no such cation exchange chromatography is required.

At this stage in the method, any remaining traces of conjugate or conjugate-derived materials are removed from the N-acetylated mixture containing the glycans, by a chromatography process. To a column of microcrystalline cellulose previously washed sequentially with water and methanol, and then extensively equilibrated in butanol, ethanol, water solvent (of composition 4:1≦0.5), the sample free of cations is applied in a solvent of composition butanol, ethanol, water of 4:1≦0.5 (v/v/v). After loading all the sample, any conjugate or conjugate-derived material is eluted away from the adsorbed glycans by use of a butanol, ethanol, water solvent (of typical composition 4:1:0.5, v/v/v), or a toluene, methanol, acetic acid solvent (of typical composition 3:1:1, v/v/v). Typically, 3–5 column volumes of wash are required to assure successful removal of such material. The glycans are then desorbed by elution with methanol, water, or a desired aqueous buffer, and the glycans so eluted are collected.

At this stage of the method, a solution exists containing the intact N- and O-glycans (originally attached to glycoconjugate) in a solvent of composition related to that used to elute the N- and O-glycans from the cellulose column, above. The N- and O-glycans at this stage consist of a mixture of authentic, unreduced, oligosaccharides and the acetohydrazone derivatives of such N- and O-glycans. Conversion of acetohydrazone derivatives to the authentic unreduced N- and O-glycans by cleavage of the acetohydrazone is achieved by exposing the N- and O-glycan mixture to mild acid, whether immobilized, mineral or Lewis acid. Various such methods have been previously reported, and are generally satisfactory. The N- and O-glycans are generally removed from solvent by evaporation, resuspended in water, and lyophilized prior to further study.

By the above method, intact, unreduced N- and O-glycans are obtained free of contaminating conjugate or conjugate-derived material in high yield from glycoconjugate containing N- and O-glycans attached via N- and O-glycosidic linkages to the conjugate. The presence of conjugate or conjugate-derived material in the final pool can be assessed by a variety of techniques, of which one such is acidic hydrolysis (6N HCl, 104° C., 60 minutes), followed by ninhydrin-based quantitation of peptide material; this is a standard procedure available to one skilled in the art.

The integrity and quantity of the N- and O-glycans can be assessed by numerous techniques. Two examples which may be used in relation to the present invention are:

(1) Composition analysis of the monosaccharides obtained from the N- and O-glycans.

(2) High-voltage paper electrophoresis and high resolution gel permeation chromatography of the reduced radiolabelled (e.g. tritiated) alditols of the N- and O-glycans.

The present invention is described, by way of example only, with reference to the accompanying Drawings and with reference to the Example.

The Drawings show:

FIG. 1: Drawing of the N- and O-glycosidic linkages attaching N- and O-glycans to a peptide.

Figure 2:
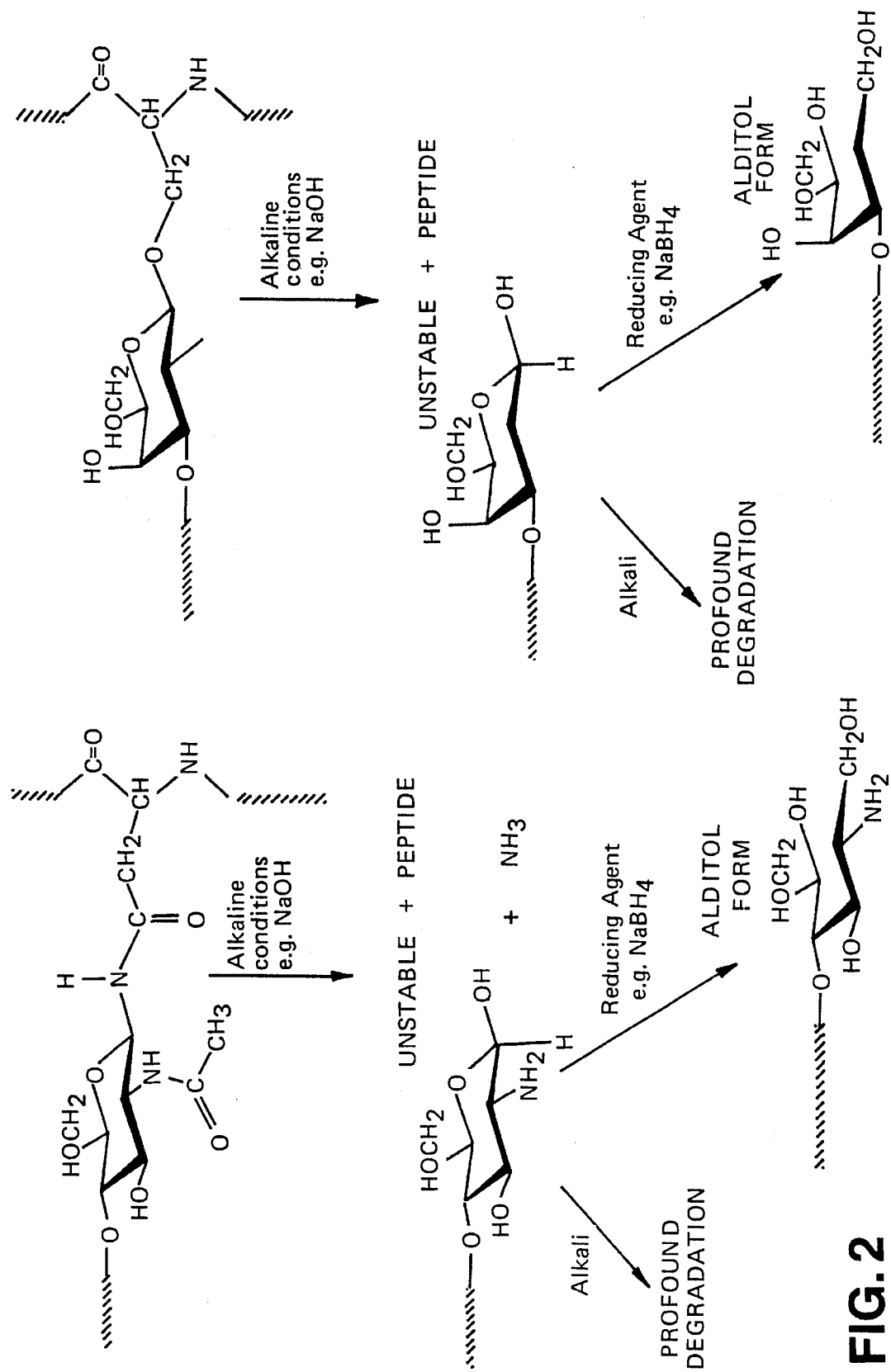

FIG. 2: Drawing summarizing the significant chemical reactions in the currently practiced method for cleavage of the N- and O-glycosidic bond by alkaline conditions.

FIG. 3: A graph summarizing the results of a study conducted to measure the effect of steady state temperature of incubation on release of N- and O-glycans from the glycoprotein bovine fetuin using an hydrazinolysis reaction.

FIG. 4: Graphs indicating the approximate range of conditions of temperature and time for recovery of defined percentages of particular glycans, under the experimental conditions discussed in this Specification.

Figure 4A:
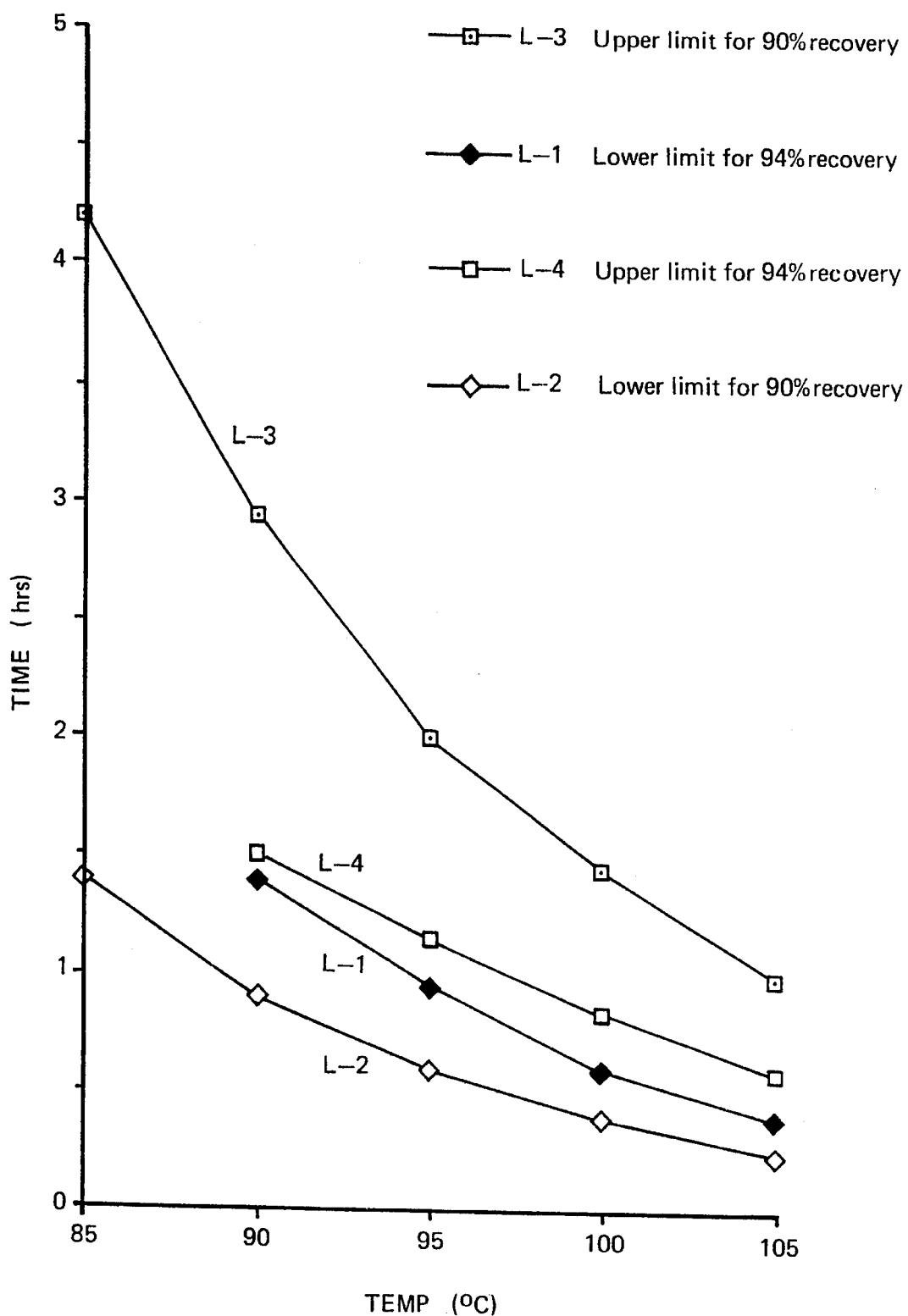

FIG. 4A: Recovery of O-glycans.

Figure 4B:
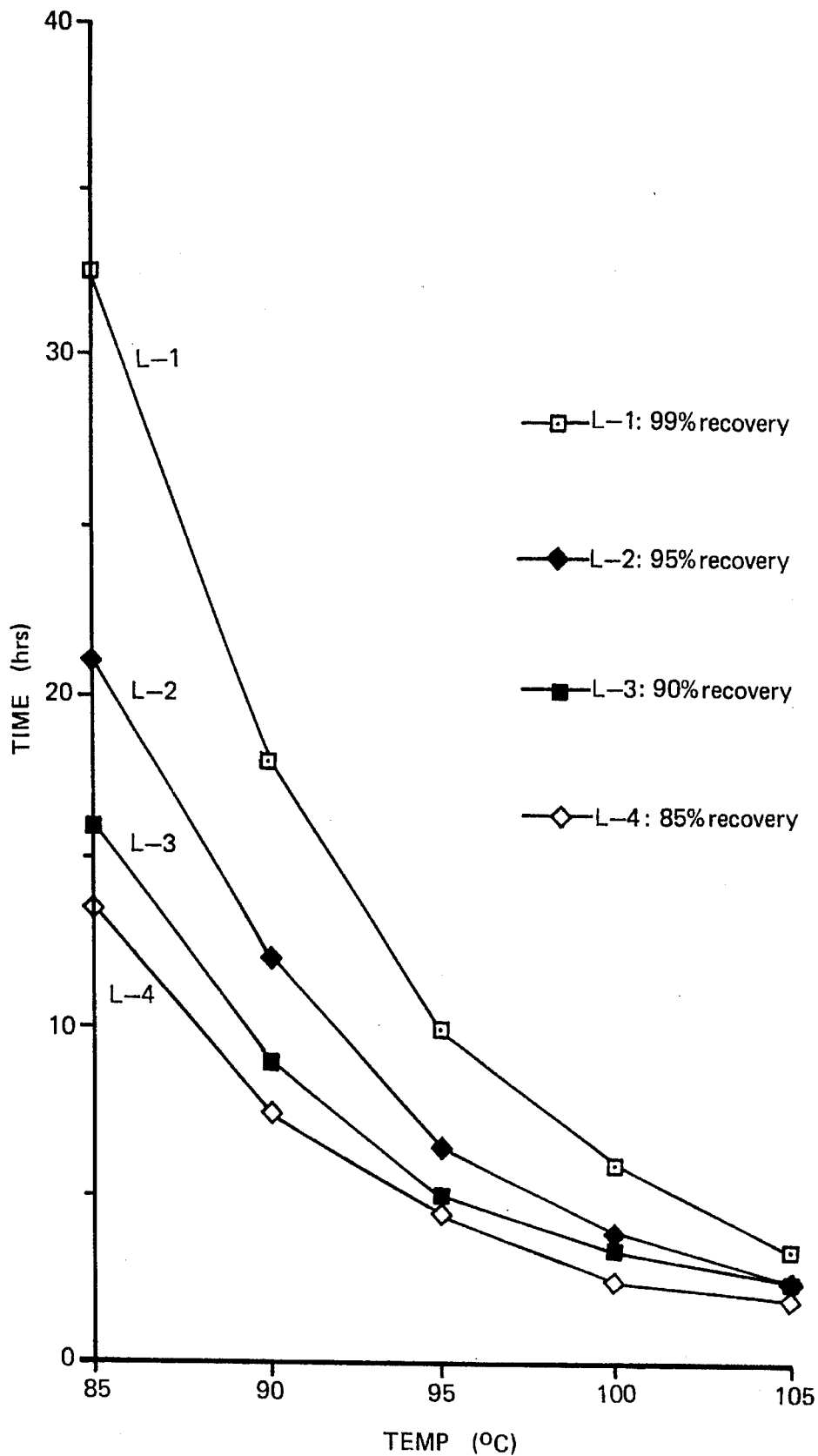
Figure 4C:
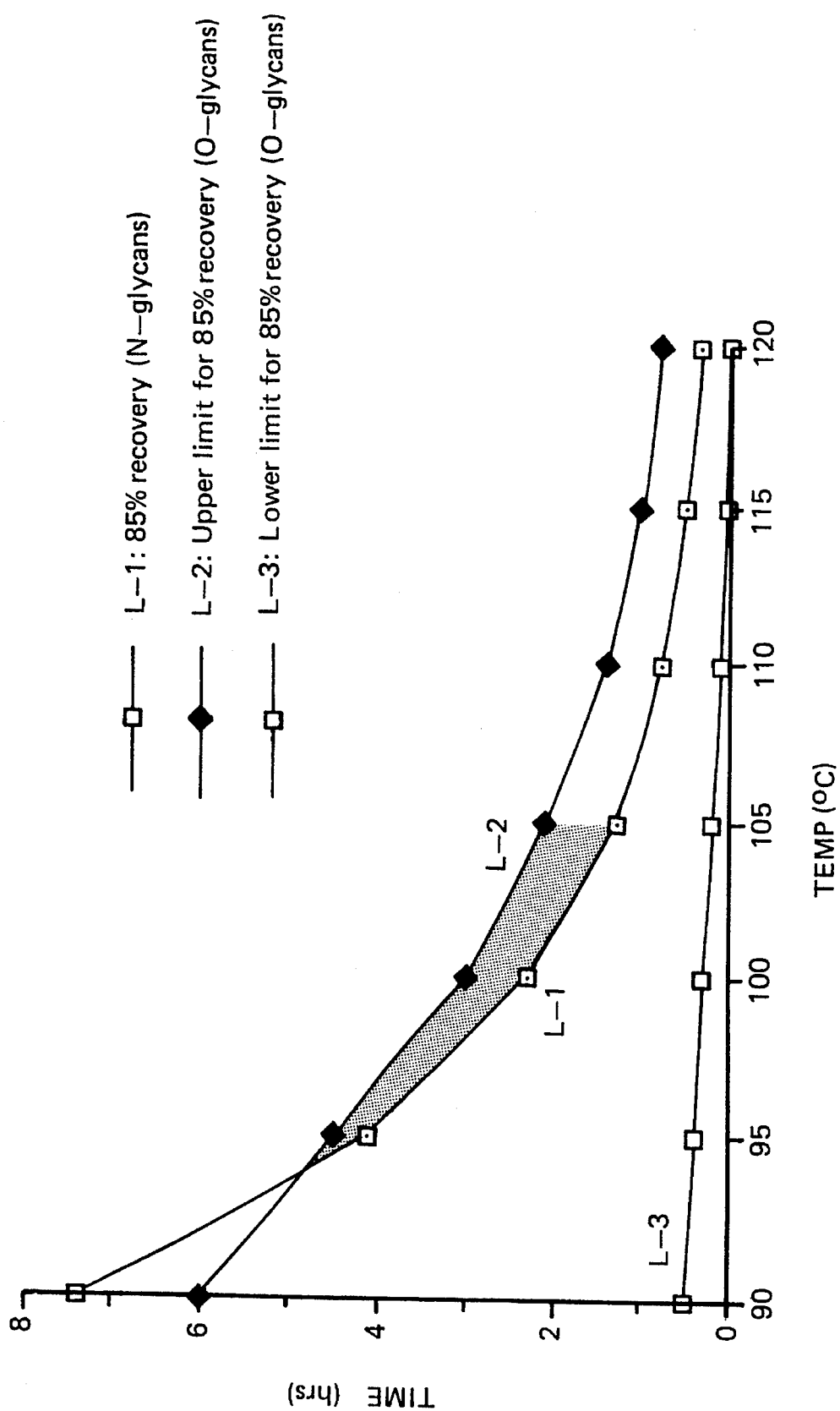

FIG. 4B: Recovery of N-glycans.

FIG. 4C: Recovery of N- and O-glycans together.

FIG. 5: A summary of the analysis of the N- and O-glycans obtained by the performance of the preferred method described in this Specification on bovine fetuin.

Figure 5A:
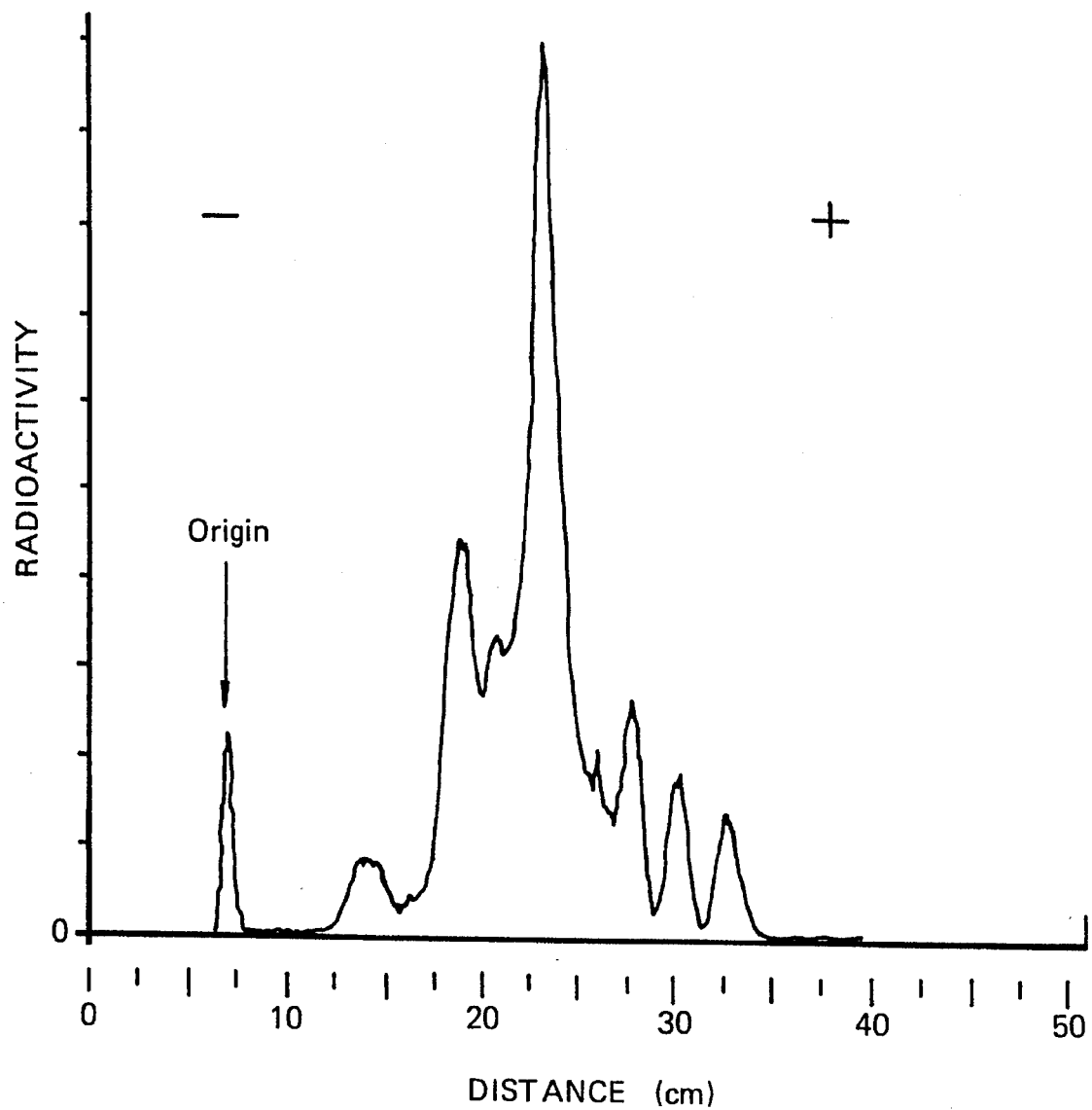

FIG. 5A: High-voltage radioelectrophoretogram of the radiolabelled glycans after deacidification.

Figure 5B:
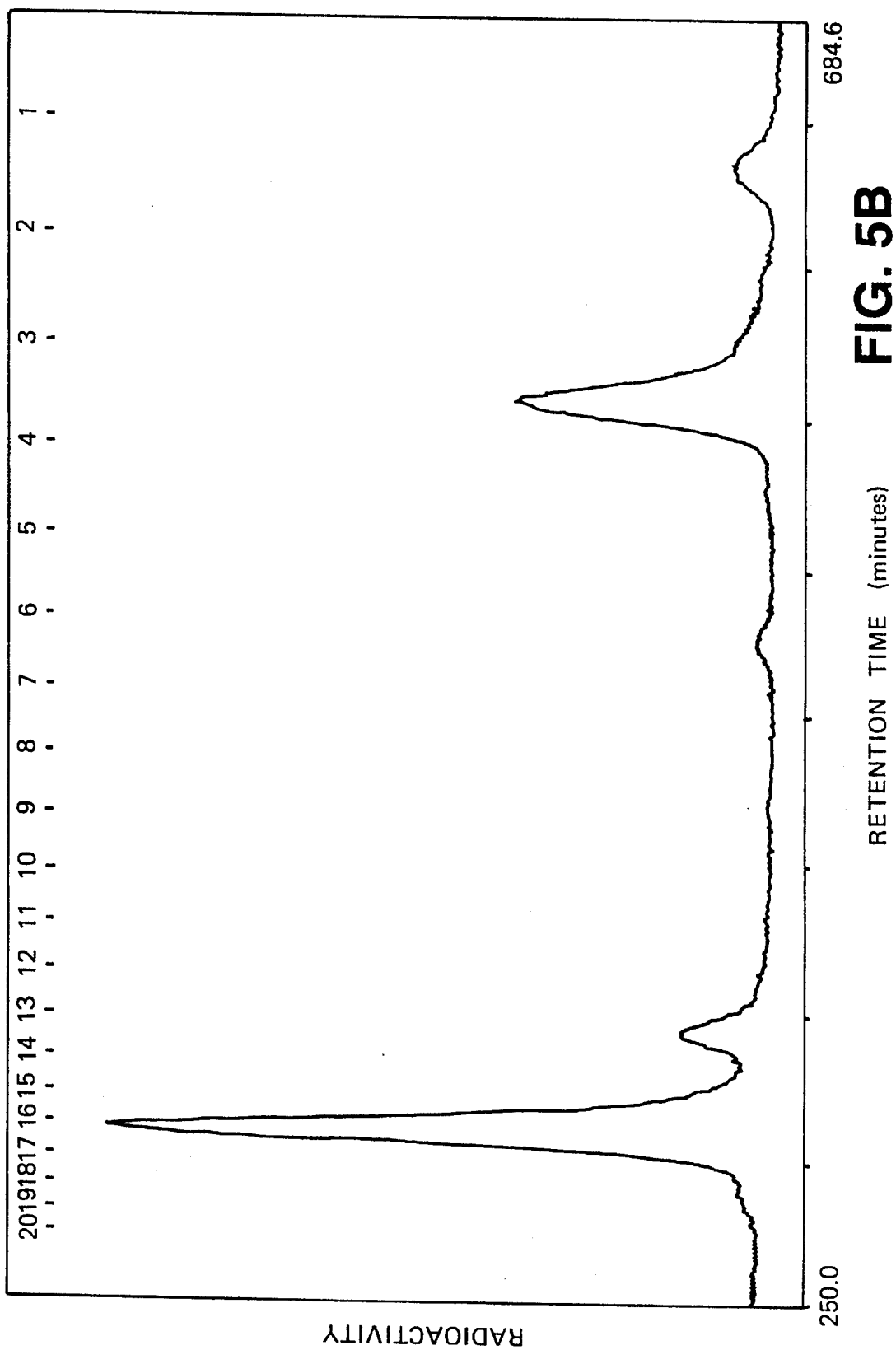

FIG. 5B: Gel filtration chromatogram of the radiolabelled glycans.

Figure 6:
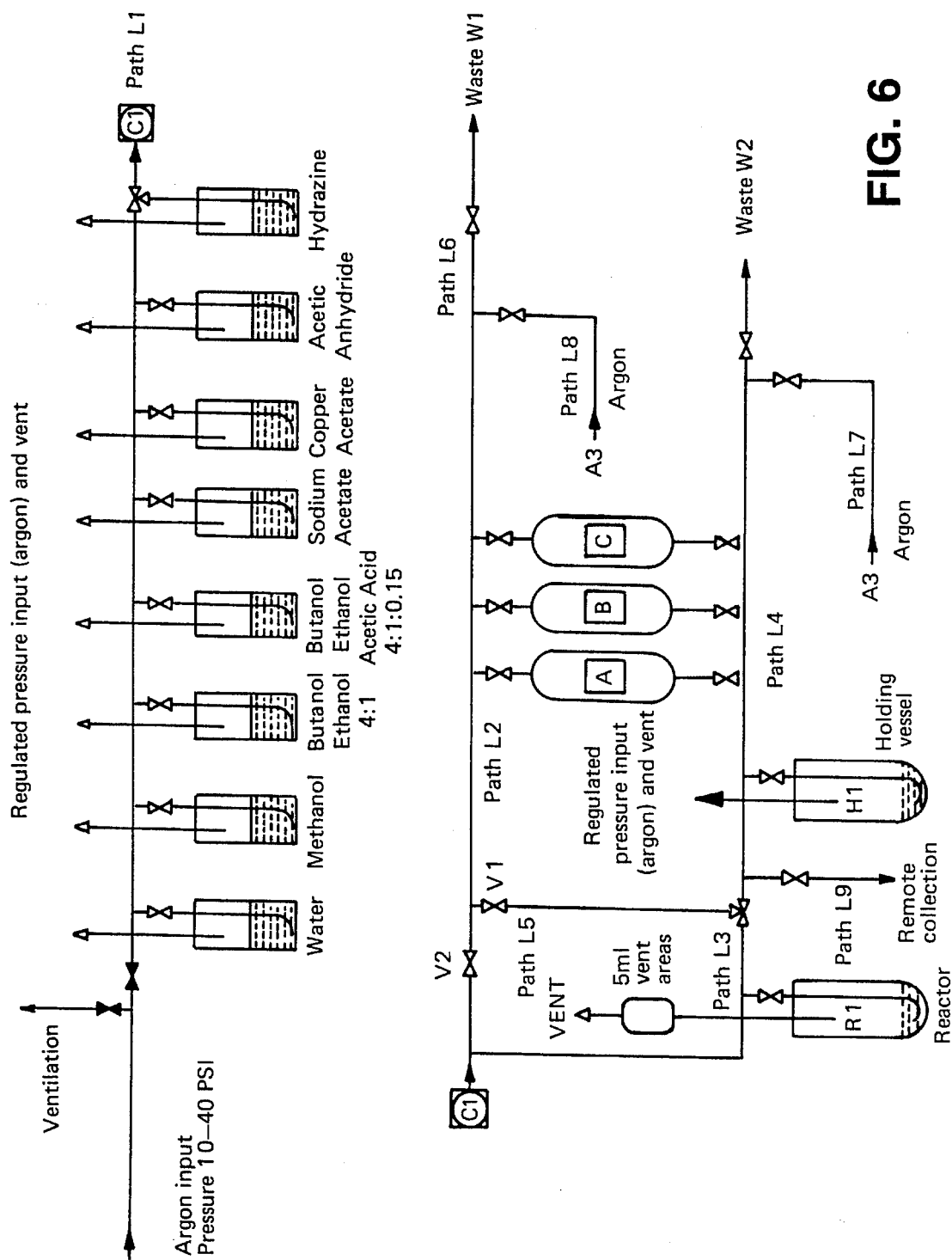

FIG. 6: A schematic diagram of an instrument shown to perform the release and/or isolation of unreduced N- and O-glycans from a glycoconjugate in an automated fasion.

EXAMPLE

Release and Isolation of N- and O-glycans from Bovine Serum Fetuin

In this example, N- and O-glycans were released from the glycoprotein bovine fetuin and the N- and O-glycans so recovered assessed with respect to integrity, yield and purity.

Fetuin from fetal calf serum was purchased from the Sigma Chemical Company, (Poole, Dorset, UK). 1 milligram of the glycoprotein was rendered salt-free by exhaustive microflow dialysis against glass-distilled water. After dialysis, the solution was lyophilized in a clean glass reaction tube using an Edwards Modulyo freeze-drier operating at 25 millibar vacuum. To the lyophilized glycoprotein was added 0.5 ml of anhydrous hydrazine (of relative water content ~2.0% v/v). The tube was sealed under an anhydrous and oxygen-free atmosphere at room temperature and then placed in an oven equilibrated at 95° C. for 3.75 hours.

After this time, unreacted hydrazine was removed from the reaction mixture in the tube or by column chromatography as follows. To the top of a pre-prepared, pre-equilibrated (in butanol, ethanol, acetic acid solvent of composition 4:1:0.15, v/v/v) column (bed volume 2 ml) of microcrystalline cellulose (Avicel®, was added 4 ml of equilibration solvent without flow. The reaction mixture from the tube (i.e. hydrazinolysate) (0.5 ml) was then added to the column, followed by thorough mixing to create a single-phase, all without flow. Liquid flow was then begun, and when all liquid had passed through the column, the column was washed with 3 column volumes of equilibration solvent. The column was next washed with 1 column volume of methanol, and then two column volumes of aqueous sodium acetate (200 mM, pH 5.0). Re-N-acetylation was performed by the addition of 0.5 ml acetic anhydride to pooled elutant and incubation at room temperature for 1 hour.

The resulting N-acetylation mixture was then passed through a Dowex AG50X12 (H$^+$) column of volume 2.2 ml, and the column was then washed with five column volumes of distilled water. The elutant and washings were combined and then rotary evaporated to dryness. The entire sample was then taken up in 0.3 ml glass distilled water and applied to the top of a column of pre-prepared, pre-equilibrated microcrystalline cellulose (0.8 cm×5 cm) containing 2.0 ml of butanol, methanol (4:1, v/v) above the cellulose bed, without flow. The aqueous phase and the butanol/ethanol phase were mixed thoroughly into a single homogeneous phase, and flow was then begun. After all the liquid had passed through, the column was washed with 5 column volumes of butanol, ethanol, water solvent (of composition 4:1:0.5, v/v/v). The column was next washed with 1 column volume of methanol and 2 column volumes of distilled water. The methanol and water fractions were co-pooled, rotary evaporated, taken up in 0.2 ml of 1 mM aqueous copper (II) acetate solution, incubated at room temperature fo 30 minutes, and passed through a tandem column of Chelex 100 (Na$^+$) and Dowex AG50X12 (H$^+$) containing 300 µl of each resin. The column was washed with five column volumes of water and the eluant and washings co-pooled, filtered (0.2 µM Teflon membrane filter), rotary evaporated to dryness, and taken up in 1 ml of glass distilled water. Aliquots of the unreduced oligosaccharide fraction were analysed for monosaccharide composition and amino acid content by the ninhydrin method. (The results are given in Table I below.) An aliquot of the unreduced oligosaccharides was radiolabelled by reduction in alkaline NaB$^3$H$_4$ and the radiolabelled oligosaccharide alditols so obtained were analyzed with respect to charge and size (after deacidification). The results are given in FIGS. 5A and 5B of the accompanying Drawings. The overall conclusion of these analyses is that contaminants other than peptide material are not detectable, that the level of peptide is <10% (by weight), and that glycans are intact, and recovered in high (e.g. ≧85%) yield.

TABLE I

|  | Total content of N-acetyl-galactosamine* (nanomoles) | Total content of N-acetyl-glucosamine* (nanomoles) | Total content of amino acids (nanomoles) |
| --- | --- | --- | --- |
| Starting Glycoprotein | 52.5 | 252.5 | 6918 |
| Final glycan pool | 45.1 | 217.2 | 332 |

*In the glycoprotein fetuin it is generally accepted that the content of N- and O-glycans is directly related to the content of N-acetylglucosamine and N-acetylgalacto-samine, respectively. The contents of N-acety-lglucosamine and N-acetylgalactosamine are therefore used as a preferred measure of the N- and O-glycan content in both the fetuin glycoprotein and the glycan pool obtained after performing the methods described in this invention.

By treating the glycoprotein bovine fetuin in accordance with the present invention, it has been established that certain sequences of processing events allow recovery with high yield (e.g. ≧85%), of intact N- and O-glycans free of contaminants. A sequence of events has been defined by which intact N- and O-glycans can be so recovered, and this sequence is such as to be readily automated. That this is so is proven by the construction and successful functioning of a machine which is able to receive a lyophilized sample of glycoconjugate and successfully deliver the intact N- and O-glycans previously associated with that glycoconjugate.

Description of the Automated Process

N- and O-linked glycans can be released from a glycoconjugate using the method of the present disclosure with the automated process shown in FIG. 6.

Note that all the vessels in the upper row, which contain respectively water, methanol, butanol/ethanol 4:1 (v/v), butanol/ethanol/acetic acid 4:1:0.15 (v/v/v), 0.2M sodium acetate solution, 0.1M copper acetate/acetic acid pH 4.0 solution, acetic anhydride (17.4M), and hydrazine are connected to a supply of anhydrous argon of commercially available grade. Desired aliquots of the contents of each vessel can be supplied along path L1 by pressurizing the relevant vessel(s) with argon through the use of the pressurized argon input line, and such delivery is under the control of the system software. In the entire process described in this Specification, all solvents and reagents are stored in, and delivered from, one of the above vessels.

The glycoconjugate under investigation is rendered substantially salt-free, for example by dialysis, gel filtration, or chromatography in a suitable system. Once salt-free, the glycoconjugate is rendered essentially anhydrous, for example by lyophilization and the water content of the sample reduced to at least that achieved at equilibrium under lyophilization conditions of 25 millibar at 25° C. The essentially anhydrous sample is put into Reactor R1 which is then connected into the automated system as shown in FIG. 6. Prior to hydrazinolysis of the sample, anhydrous argon is first passed over the sample along Path L1, L3 to substantially replace the air in Reactor R1 with argon. Hydrazine of relative water content ≦2.0% (v/v) is then delivered to Reactor R1 along path L1, L3 from the hydrazine containing vessel shown connected to path L1 prior to point C1, as shown in the upper part of the FIG. 6.

Release of N- and O-glycans

Following delivery of the aliquot of hydrazine to R1, the hydrazinolysis reaction leading to release of N- and O-linked glycans is performed by raising the temperature in Reactor R1 (through the use of a surrounding heating element) for a time selected to accord with the present invention; typically 95° C. for 3.75 hours, at which point the reaction mixture is allowed to cool towards ambient temperature.

Isolation of N- and O-glycans

Hydrazine Removal from Released Glycans

In order to remove any unreacted hydrazine by a chromatographic process the contents of the Reactor R1 is transferred in aliquots under argon pressure along path L3, L5, L2 to chromatography column A (containing a cellulose-based medium, such as microcrystalline cellulose) and during this latter passage, is mixed with a solvent of butanol, ethanol and acetic acid 4:1:0.15 (v/v/v), (delivered along path L1), using valves V1 and V2, at an approximate ratio of 5% contents of R1 to 95% solvent (v/v), and the mixture is passed through column A to waste W2. A further 3 ml of the solvent of composition butanol, ethanol and acetic acid 4:1:0.15 (v/v/v) is then delivered to the Reactor R1 along path L1, L3, and from there to column A along path L3, L5, L2 with the column outlet again directed to waste W2. This is repeated with 6 ml of the same solvent to ensure that all traces of hydrazine are removed from the Reactor R1. A volume of 6 ml of the solvent of composition butanol, ethanol 4:1 (v/v) is delivered to the Reactor R1 along path L1, L3 and from there to column A along path L3, L5, L2 to remove any acetic acid present in column A, with the outlet of column A still connected to waste W2.

N-acetylation of Any de-N-acetylated Glycans

To perform the re-N-acetylation, 0.2 ml of acetic anhydride is delivered to the Reactor R1 along path L1, L3, and then to column A along path L3, L5 and L2 and during this latter passage, it is mixed with the solvent butanol, ethanol 4:1 (v/v) (delivered along path L1), using valves V1 and V2, at an approximate ratio of 5% acetic anhydride to 95% solvent (v/v), and the mixture is passed through column A to waste W2. This delivery, and the N-acetylation reaction is continued for 30 minutes. At the end of this period, to remove excess acetic anhydride, 3 ml of the solvent butanol, ethanol 4:1 (v/v) is delivered to column A along path L1, L2.

In all operations the outlet from Column A is directed to waste W2. At the end of this step, N- and O-glycans and conjugate or conjugate-derived material are adsorbed to the cellulose of column A.

Separation of Glycans from Conjugate Material

In order to remove conjugate or conjugate-derived material a volume of 0.5 ml water is delivered to the Reactor R1 via path L1, L3. The contents of R1 are then mixed with the solvent butanol, ethanol 4:1 (v/v), (delivered along path L1), by using valves V1 and V2, at an approximate ratio of 5% water to 95% solvent (v/v) to form a solvent mixture of composition butanol, ethanol and water 4:1:0.25 (v/v/v), and this solvent is passed through column A, with the outlet of column A connected to waste W2.

Desorption of the N- and O-glycans from the cellulose of column A then takes place as follows. Methanol, (0.2 ml) is passed along path L1, L2, through the column A, in 4 pulses (of 50 μl aliquots each), each pulse being immediately followed with an argon pulse, with the outlet of column A connected to the holding vessel (H1) by path L4. The sodium acetate solution (3.0 ml) is then passed to column A with similar pulses of argon along path L1, L2, with the outlet of column A still connected to the holding vessel H1.

To ensure complete re-N-acetylation of the N- and O-glycans a volume of acetic anhydride (0.1 ml) is then passed along path L1, L3, L4 to the holding vessel H1, and the reaction mixture left for 30 minutes at ambient temperature.

Regeneration of Intact, Unaltered Glycans

To replace $Na^+$ ions with $H^+$ ions, the contents of the holding vessel (H1) are then passed along path L4 through the chromatography column B, containing a bed of 1.0 ml Dowex Ag50X12 ($H^+$), and through column B directly to the Reactor R1 through path L2, L5, L3. To achieve glycan-acetohydrazone cleavage, and so regenerate intact and unaltered glycans, a solution of 0.2 ml of copper acetate is then delivered to the Reactor R1 through path L1, L3, and the reaction mixture left for 60 minutes at ambient temperature. To replace $Cu^{2+}$ ions with $H^+$ ions, the mixture is then passed from R1 through the chromatography column C containing a mixture of 0.5 ml of each of Chelex 100 ($Na^+$) and of Dowex AG50X12 ($H^+$), along path L3, L5, L2, to the remote collection port through path L4, L9. A volume of 1 ml of water is then delivered to the Reactor R1 along path L1, L3 for washing purposes, and then through column C to the remote collection port through path L3, L5, L2, L4, L9. The solutions received at the remote collection port contain the released intact N- and O-glycans in a solution of dilute acetic acid, and may be removed from the instrument for further analysis.

We claim:

1. A method for releasing N- and O-glycans from a glycoconjugate comprising both N- and O-glycans which method comprises reacting said glycoconjugate with a hydrazine reagent, said glycoconjugate being essentially salt-free and essentially anhydrous and said hydrazine reagent being essentially anhydrous, and controlling the time and temperature conditions under which the glycoconjugate is reacted with the hydrazine reagent within a range, according to first-order kinetics, corresponding to about 95° C. to about 105° C., so as to release at least 85% of the total N- and O-glycans from the glycoconjugate recoverable in substantially unreduced and intact form.

2. A method as claimed in claim 1 for releasing unreduced and intact N- and O-glycans from glycoconjugates comprising heating an essentially salt-free and essentially anhydrous conjugate with essentially anyhdrous hydrazine reagent under conditions to release from the conjugate N- and O-glycans recoverable in intact form.

3. A method as claimed in claim 1 which includes the additional step of isolating said released intact and unreduced N- and O-glycans.

4. A method as claimed in claim 1 wherein the glycoconjugate is selected from the group consisting of a glycoprotein, a glycohormone, and a glycolipid.

5. A method as claimed in claim 1 wherein the method additionally includes the step of removing salt from the glycoconjugate prior to reacting the glycoconjugate with the hydrazine reagent.

6. A method as claimed in claim 5 wherein salt is removed from a glycoconjugate by dialysis, gel filtration or chromatography.

7. A method as claimed in claim 1 wherein the method also includes the step of removing water from the glycoconjugate prior to reacting the glycoconjugate with the hydrazine reagent.

8. A method as claimed in claim 7 wherein water is removed from a glycoconjugate by lyophilization.

9. A method as claimed in claim 8 where water is removed to at least equilibrium water content under lyophilization conditions of 25 millibar at 25° C.

10. A method as claimed in claim 1 wherein the hydrazine reagent is hydrazine, hydrazine vapor or a hydrazine-containing compound.

11. A method as claimed in claim 1 wherein the glycoconjugate and the hydrazine reagent are brought together and the resulting reaction mixture is heated.

12. A method as claimed in claim 1 wherein an acetohydrazine derivative of the N- and O-glycans is subjected to acidic conditions to generate unreduced N- and O-glycan.

13. A method as claimed in claim 1 wherein the hydrazine reagent has a water content not exceeding 4% volume/volume.

14. A method as claimed in claim 1 wherein the glycoconjugate is bovine serum fetuin.

15. A method as claimed in claim 1 wherein intact N- and O-glycans are released from a glycoconjugate by incubation with hydrazine at 95° C. for 3.75 hours.

16. A method for releasing and isolating N- and O-glycans from a glycoconjugate comprising both N- and O-glycans comprising the steps of:

a) reacting a glycoconjugate with a hydrazine reagent to release unreduced N- and O-glycans and reduced N- and O-glycans from said glycoconjugate, said glycoconjugate being essentially salt-free and essentially anhydrous and said hydrazine reagent being essentially anhydrous, and controlling the time and temperature conditions under which the glycoconjugate is reacted with the hydrazine reagent within a range, according to first-order kinetics, corresponding to about 85° C. to about 105° C., at 8 hours to cause release of the N- and O-glycans from the glycoconjugate recoverable in essentially unreduced intact form;

b) contacting the reaction mixture of step (a) with a first chromatographic material to sorb the N- and O-glycans, and reduced N- and O-glycans, upon the chromatographic material;

c) eluting the first chromatographic material to separate the unreduced N- and O-glycans or reduced N- and O-glycans from conjugate or conjugate-derived material and removing any hydrazine reagent;

d) removing N- and O-glycans from the mixture of step (c) by sorption upon a second chromatographic material and selective elution of N- and O-glycans from the second chromatographic material; and thereafter e) converting any reduced N- and O-glycans present to unreduced N- and O-glycans.

17. The method of claim 16 wherein any N- and O-glycan derivatives having free primary amino acid groups present are, in an additional step, N-acetylated to generate unreduced glycan from the derivative.

18. A method as claimed in claim 17 wherein an N-acetylation reaction is performed before desorption from the first chromatographic material.

19. A method as claimed in claim 17 wherein an N-acetylation reaction is performed after desorption from the first chromatographic material.

20. The method of claim 17 including the further step of removing mono- or di-valent cations from the reaction mixture after the N-acetylation reaction.

* * * * *